(12) United States Patent
Feler

(10) Patent No.: US 8,774,940 B2
(45) Date of Patent: Jul. 8, 2014

(54) PADDLE LEAD BODY WITH INSERTION TAB

(71) Applicant: Advanced Neuromodulation Systems, Inc., Plano, TX (US)

(72) Inventor: Claudio Feler, Carbondale, CO (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 13/788,944

(22) Filed: Mar. 7, 2013

(65) Prior Publication Data

US 2013/0238076 A1    Sep. 12, 2013

Related U.S. Application Data

(60) Provisional application No. 61/608,372, filed on Mar. 8, 2012.

(51) Int. Cl.
*A61N 1/05* (2006.01)

(52) U.S. Cl.
USPC .......................................................... 607/116

(58) Field of Classification Search
None
See application file for complete search history.

(56) References Cited

U.S. PATENT DOCUMENTS

| | | | | |
|---|---|---|---|---|
| 3,738,368 | A * | 6/1973 | Avery et al. .................. | 607/117 |
| 7,155,287 | B2 * | 12/2006 | Gavronsky ..................... | 607/46 |
| 7,499,742 | B2 * | 3/2009 | Bolea et al. ..................... | 600/372 |
| 2008/0228250 | A1 * | 9/2008 | Mironer ........................ | 607/117 |
| 2009/0099439 | A1 * | 4/2009 | Barolat .......................... | 600/372 |
| 2009/0112301 | A1 * | 4/2009 | Kowalczyk .................... | 607/117 |

* cited by examiner

*Primary Examiner* — Brian T Gedeon

(57) ABSTRACT

An implantable stimulation system including an epidural lead for spinal cord stimulation that includes a paddle having an array of electrodes coupled to conductors within the paddle body. The paddle is elongated in shaped with the distal end of the paddle having a tabbed or extended portion with the lead exiting the extended portion of the paddle an angle relative to the longitudinal axis of the paddle.

18 Claims, 3 Drawing Sheets

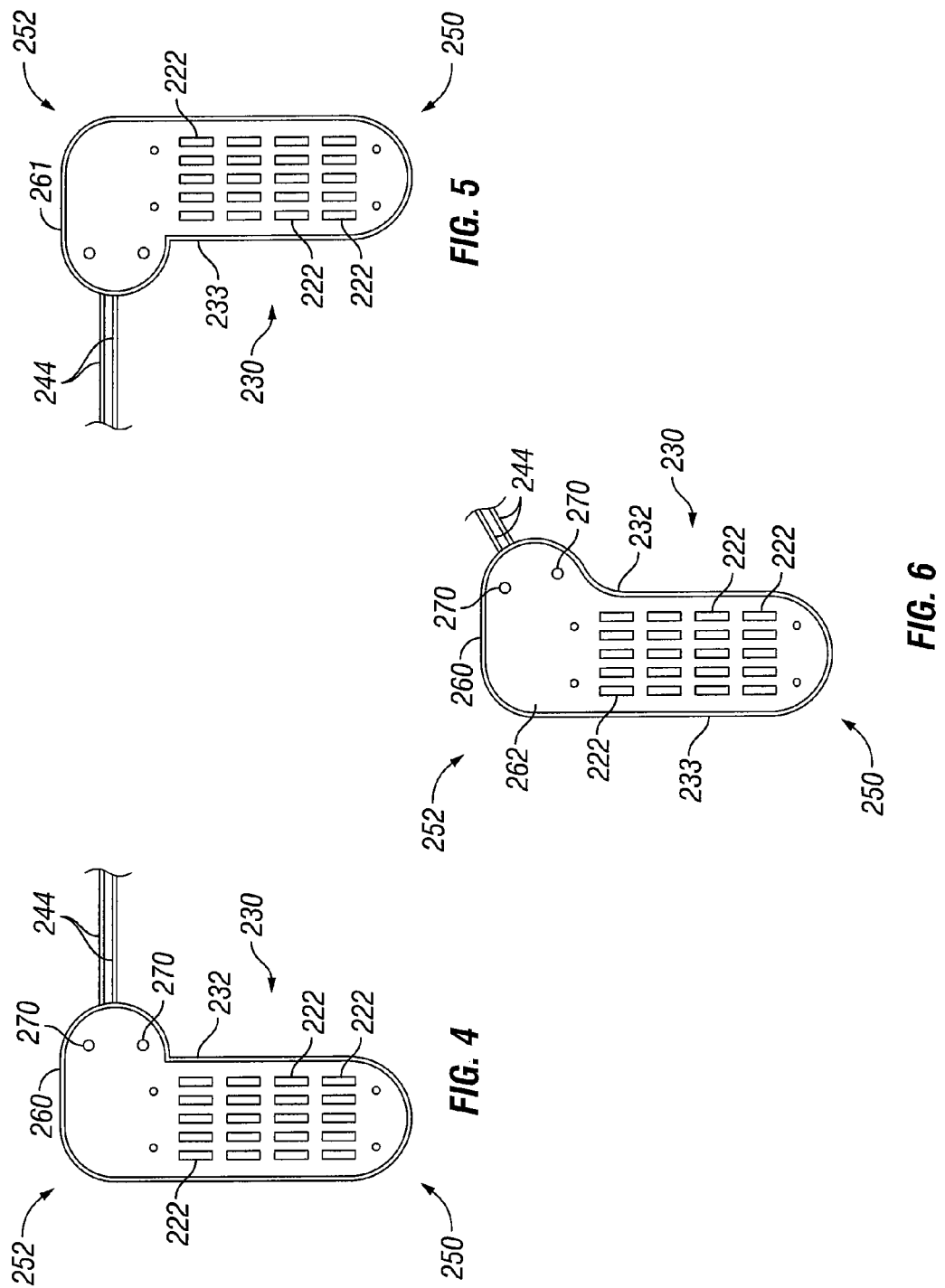

PADDLE LEAD BODY WITH INSERTION TAB

CROSS REFERENCE TO RELATED APPLICATIONS

This application claims the benefit of U.S. Provisional Application No. 61/608,372, filed Mar. 8, 2012, the disclosures of which are fully incorporated herein by reference for all purposes.

TECHNICAL FIELD

The present application relates generally to implantable medical stimulators and more particularly to a paddle lead having a plurality of electrodes wherein the lead is shaped to facilitate the insertion of paddle lead within the epidural space.

BACKGROUND

Neurostimulation systems are devices that generate electrical pulses and deliver the pulses to nerve tissue to treat a variety of disorders. Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is coupled to one or more stimulation leads through electrical connections provided in a "header" of the pulse generator. Specifically, feedthrough wires typically exit the metallic housing and enter into a header structure of a moldable material. Within the header structure, the feed-through wires are electrically coupled to annular electrical connectors. The header structure holds the annular connectors in a fixed arrangement that corresponds to the arrangement of terminals on a stimulation lead.

Spinal cord stimulation (SCS) is an example of neurostimulation in which electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Also, each exterior region, or each dermatome, of the human body is associated with a particular spinal nerve root at a particular longitudinal spinal position. The head and neck regions are associated with C2-C8, the back region extends from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position.

Positioning of an applied electrical field relative to a physiological midline is also important. Nerve fibers extend between the brain and nerve root along the same side of the dorsal column as the peripheral areas of the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral." Accordingly, bilateral pain is addressed through application of electrical energy along both sides of the column and/or along a patient's physiological midline.

Percutaneous leads and laminotomy leads are the two most common types of lead designs that provide conductors that deliver stimulation pulses from an implantable pulse generator (IPG) to distal electrodes adjacent to the nerve tissue. As shown in FIG. 1A, conventional percutaneous lead 100 includes electrodes 101 that substantially conform to the body of the body portion of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

As shown in FIG. 1B, conventional laminotomy or paddle lead 150 has a paddle configuration and typically possesses a plurality of electrodes 151 arranged in one or more columns. Multi-column laminotomy leads enable reliable positioning of a plurality of electrodes. Also, laminotomy leads offer a more stable platform that tends to migrate less after implantation and that is capable of being sutured in place. Laminotomy leads also create a uni-directional electrical field and, hence, can be used in a more electrically efficient manner than conventional percutaneous leads. Due to their dimensions and physical characteristics, conventional laminotomy leads require a surgical procedure for implantation. The surgical procedure (a partial laminectomy) is evasive and requires the resection and removal of certain vertebral tissue to allow both access to the dura and proper positioning of a laminotomy lead.

SUMMARY

Some representative embodiments are directed to the use of a paddle structure to apply electrical stimulation to spinal nervous tissue to treat a variety of diseases and/or conditions, for example pain or chronic pain. A stimulation paddle lead is implanted in the patient with electrodes in the epidural space of the patient. The paddle portion of the paddle lead is elongated shaped with the distal end of the paddle having a tabbed or extended portion with the leads exiting the extended portion of the paddle an angle relative to the longitudinal axis of the paddle.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiments disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 4 depicts a stimulation paddle according to another representative embodiment.

FIG. 5 depicts a stimulation paddle according to yet another representative embodiment.

FIG. 6 depicts a stimulation paddle according to another representative embodiment.

DETAILED DESCRIPTION

Figure 1A:
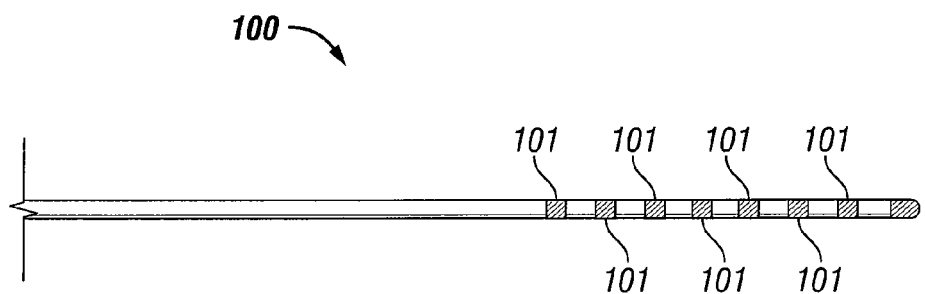
FIGS. 1A and 1B depict a conventional percutaneous lead and a convention paddle lead.
Figure 1B:
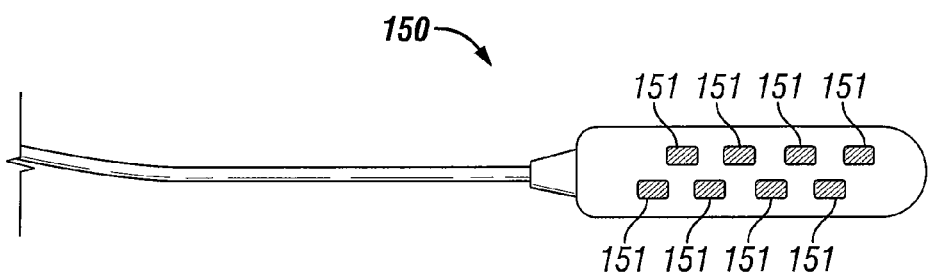
Figure 2:
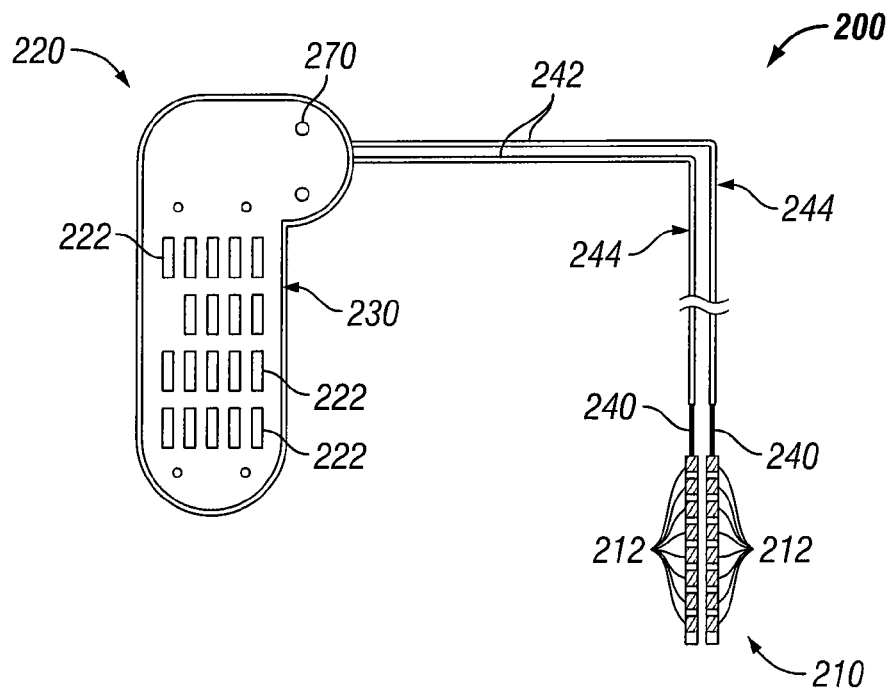
FIG. 2 depicts a planar view of a paddle lead according to one representative embodiment.

Referring now to FIG. 2, there is depicted a laminotomy lead 200 that can be used for spinal cord stimulation or stimulation of spinal nervous tissue to treat a variety of diseases and/or conditions, for example, but not limited to pain (e.g., peripheral pain), more specifically chronic pain, CRSII or CRSI. Laminotomy or paddle lead 200 includes proximal end 210 and distal end 220. Proximal end 210 includes a plurality of electrically conductive terminals 212. Distal end 220 includes a plurality of electrically conductive electrodes 222 (only 3 of the electrodes have been annotated for the sake of clarity) arranged within a flat, thin, paddle-like structure 230. The electrodes 220 are mutually separated by insulative material of the paddle. The paddle structure 230 itself may have a width such that it spans the entire dorsal column or fits within the epidural space. Those of skill in the art are cognizant that the size of the dorsal column and epidural space can vary among individuals as well as within an individual. Thus, depending upon the desired implantation site, thoracic or cervical, a paddle structure may be designed to fit into the desired space such that it at least covers the anatomical and physiological midline of the patient.

Since the paddle structure 230 can be as wide as the dorsal column or epidural space, the electrodes 222 likewise may have a width such that the combination of the size and number of electrodes span the width of paddle. The width of the electrode array can be a width that spans the anatomical and physiological midline. The length of the electrodes may vary as well such that the length comprises a length that is appropriate for the length of the paddle structure. In one such example, but not by way of limitation, the paddle structure 230 has a width of about 11 mm with the electrodes 222 having an approximate width of about 0.5 mm to about 1.5 mm, or any range there between, more particularly; the width of the electrode can be about 1 mm having an approximate electrode array width of about 9 mm.

Yet further, the spacing of the electrodes 222 may vary as well depending upon the paddle structure and the desired usage or placement of the structure. For a paddle structure 230 adapted for implantation within a cervical vertebral level, good results have been achieved with the electrodes being spaced apart approximately 1.5 mm laterally and 2.5 mm longitudinally. For a paddle structure 230 adapted for implantation within a thoracic vertebral level, good results have been achieved with the electrodes 222 being spaced apart by 1.0 mm laterally and 2 mm to 3 mm longitudinally. Conductors 240 (which are embedded within the insulative material of the lead body) electrically connect electrodes 222 to terminals 212.

Terminals 212 and electrodes 222 are preferably formed of a non-corrosive, highly conductive material. Examples of such material include stainless steel, MP35N, platinum, and platinum alloys. In a preferred embodiment, terminals 212 and electrodes 222 are formed of a platinum-iridium alloy. Each conductor 240 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, a preferred embodiment uses conductors 240 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of representative embodiments, such insulative material protects the individual conductors 240 if its respective sheath 242 was breached during use.

In addition to providing the requisite strength, flexibility, and resistance to fatigue, conductors 240 formed of multi-strands of drawn-filled tubes, in accordance with the above description, provide a low resistance alternative to other materials. Specifically, a stranded wire, or even a coiled wire, of approximately 60 cm and formed of MP35N or stainless steel or the like would have a measured resistance in excess of 30 ohms. In contrast, for the same length, a wire formed of multi-strands of drawn-filled tubes could have a resistance less than 4 ohms.

Sheaths 242 and paddle structure 230 are preferably formed from a medical grade, substantially inert material, for example, polyurethane, silicone, or the like. Importantly, such material should be non-reactive to the environment of the human body, provide a flexible and durable (i.e., fatigue resistant) exterior structure for the components of paddle lead 200, and insulate adjacent terminals 212 and/or electrodes 222. Additional structure (e.g., a nylon mesh, a fiberglass substrate) (not shown) can be internalized within the paddle structure 230 to assume a prescribed cross-sectional form.

Figure 3:
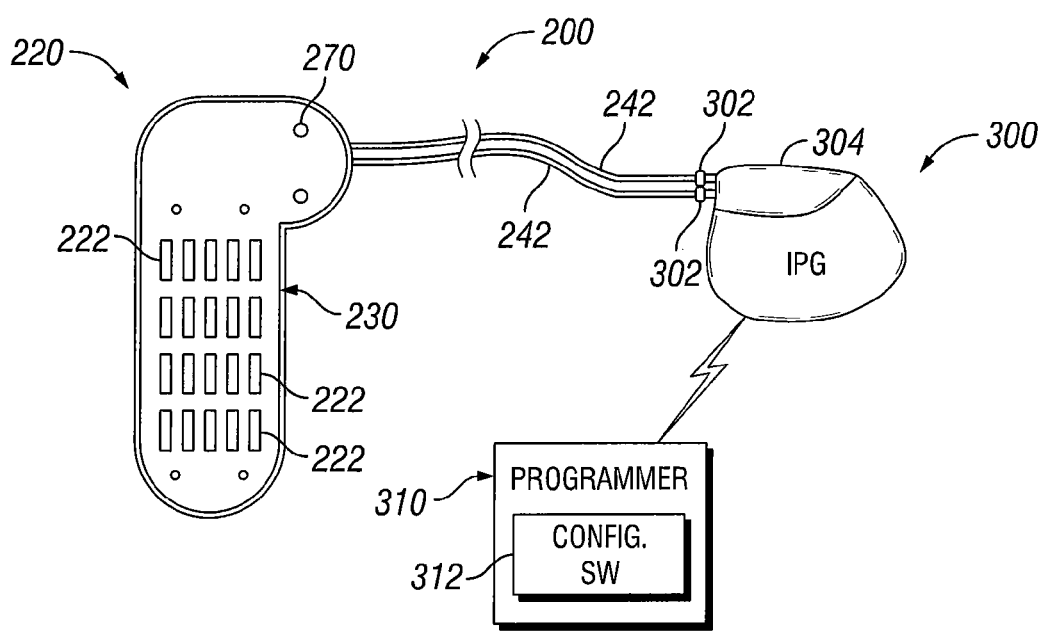
FIG. 3 depicts a system for implantable pulse generator with a paddle lead in communication with a wireless programming device according to one representative embodiment.

FIG. 3 depicts paddle lead 200 coupled to IPG 300 which is in wireless communication with programmer device 310. An example of a commercially available IPG is the Eon™ Rechargeable IPG manufactured by Advanced Neuromodulation Systems, Inc, although any suitable IPG, such as RF powered devices, could be alternatively employed. As shown in FIG. 3, paddle lead 200 is coupled to the headers ports 302 of IPG 300. Each header port 302 electrically couples the respective terminals 212 (shown in FIG. 2) to a switch matrix (not shown) within IPG 300.

The switch matrix selectively connects the pulse generating circuitry (not shown) of IPG 300 to the various terminals 212, and, hence to the electrodes 222. The sealed portion 304 of IPG 300 contains the pulse generating circuitry, communication circuitry, control circuitry, and battery (not shown) within an enclosure to protect the components after implantation within a patient. The control circuitry may comprise a microprocessor, one or more ASICs, and/or any suitable circuitry for controlling the pulse generating circuitry. The control circuitry controls the pulse generating circuitry to apply electrical pulses to the patient via electrodes 222 of paddle lead 200 according to multiple pulse parameters (e.g., pulse amplitude, pulse width, pulse frequency, etc.). The electrodes 222 are set to function as cathodes or anodes or set to a high-impedance state for a given pulse according to the couplings provided by the switch matrix. The electrode states may be changed between pulses.

When paddle lead 200 is initially implanted within the patient, a determination of the set(s) of pulse parameters and the electrode configuration(s) that effectively treat the patient's condition is made. The determination or programming typically occurs through a physician's interaction with configuration software 312 executed on the programmer device 310. Configuration software 312 steps the physician through a number of parameters and electrode configurations. In preferred embodiments, the electrode configurations are stepped through by laterally "steering" the electrical field by moving the anodes and/or cathodes along a row of the paddle as discussed above. The patient provides feedback to the physician regarding the perceived stimulation that occurs in response the pulse parameters and electrode configuration(s). The physician effects changes to the parameters and electrode configuration(s) until optimal pulse parameters and electrode configuration(s) are determined. The final pulse parameters and configurations are stored within IPG 300 for subsequent use. The pulse parameters and configurations are used by IPG 300 to control the electrical stimulation provided to the patient via paddle lead 200.

As depicted in FIG. 4, paddle structure 230 includes an array of electrodes 222 that are spaced apart longitudinally along the length of paddle structure 230 from end 250 towards end 252, and are spaced apart across the width of paddle structure 230. The spacing of the electrodes 222 can be set accordingly to the target implant site and the needed stimulation. Paddle structure 230 further includes suture holes 270 which permit the suturing of paddle structure 230 to the patient after implantation to help anchor the paddle lead 200 at the target location.

Paddle structure 230 includes a tabbed or extended curved portion 260 that extends generally perpendicular from the length side 232 at end 252 of paddle structure 230. Leads 244 are connected to paddle structure 230 at tabbed portion 260 and connect thereto in a generally perpendicular manner with respect to the length of paddle structure 230.

While tabbed portion 260 is depicted as a generally uniform curved shaped, those skilled in the art will recognize that tabbed portion 260 could be shaped to more particularly conform to a user's preference or to further conform to the targeted epidural space.

Referring now to FIG. 5, there is depicted another representative embodiment of a paddle structure 230. As with the embodiment illustrated in FIG. 4, paddle structure 230 includes an array of electrodes 222 that are spaced apart longitudinally along the length of paddle structure 230 from end 250 towards end 252, and are spaced apart across the width of paddle structure 230. The spacing of the electrodes 222 can be set accordingly to the target implant site and the needed stimulation.

Paddle structure 230 includes a tabbed or extended curved portion 261 that extends generally perpendicular from the length side 233 (opposite side 232 of FIG. 4) at end 252 of paddle structure 230. Leads 244 are connected to paddle structure 230 at tabbed portion 260 and connect thereto in a generally perpendicular manner with respect to the length of paddle structure 230.

As with the embodiment depicted in FIG. 4, while tabbed portion 260 is depicted as a generally uniform curved shaped, those skilled in the art will recognize that tabbed portion 260 could be shaped to more particularly conform to a user's preference or to further conform to the targeted epidural space.

Referring now to FIG. 6, there is depicted another representative embodiment of a paddle structure 230. As with the embodiments illustrated herein above, paddle structure 230 includes an array of electrodes 222 that are spaced apart longitudinally along the length of paddle structure 230 from end 250 towards end 252, and are spaced apart across the width of paddle structure 230. The spacing of the electrodes 222 can be set accordingly to the desired target implant site and the desired stimulation.

Paddle structure 230 includes a tabbed or extended curved portion 262 that extends at an obtuse angle with respect to the length of the paddle structure 230 from the side 233 (opposite side 232 of FIG. 4) at end 252 of paddle structure 230. Leads 244 are connected to paddle structure 230 at tabbed portion 260 and connect thereto also at an obtuse angle with respect to the length of paddle structure 230.

As with the embodiment depicted above, while tabbed portion 262 is depicted as a generally uniform curved shaped, those skilled in the art will recognize that tabbed portion 262 could be shaped to more particularly conform to a user's preference or to further conform to the targeted epidural space. In addition, it is anticipated that tabbed portion 262 could extend from side 233.

When paddle lead 200 is to be implanted within a patient, a laminotomy is performed on the patient wherein at least a portion of the lamina of the vertebral bone is removed to provide access to the epidural space at the site of the target insertion of paddle lead 200. The implanter holds the paddle structure 230, at least partially by the tabbed portion (260, 261, 262) to facilitate the insertion of paddle structure 230, into the epidural space of the patient so that the electrodes 222 are placed over the midline of the spinal cord, with end 250 being inserted first.

The tabbed portion (260, 261, 262) along with the configuration of the connection of leads 244 to paddle structure 230 facilitate the insertion of the paddle structure 230 into the epidural space, at least in part, by permitting the implanter to easily grab paddle portion 230 from the side at the tab (260, 261, 262) and line-up the midline of the paddle structure 230 with the midline of the spinal cord while also permitting implanter's hand to be offset from the midline of the spinal cord. Additionally, leads 244 being connected to the tabbed portion (260, 261, 262) and extending from the paddle structure 230 at an angle with respect to the longitudinal midline of paddle portion 230 substantially reduces or even eliminates interference caused from close proximity of the contiguous vertebrae at the site of the laminectomy.

In addition to facilitating the implantation of the paddle portion 230 of paddle lead 200 into the epidural space, the configuration of the connection of the leads 244 to the paddle portion 230 at an angle with respect to the longitudinal midline of paddle portion 230 inhibits the movement or migration of paddle portion 230 after completion of the implantation as the leads 244 to not have to be bent around the adjacent lamina at the site of the laminectomy.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed:

1. A medical lead system for delivering electrical stimulation to tissue of a patient, the medical lead system comprising:
   a lead body for conducting electrical pulses through a plurality of conductors;
   a paddle having a distal end and proximate end, first side and a second side spaced apart by a width of the paddle, and a longitudinal axis extending between the distal end and the proximate end;
   a plurality of electrodes integrated with the paddle, with a portion of each of the plurality of electrodes being exposed at a face of the paddle, each of the plurality of electrodes being electrically connected to each of the plurality of conductors, the plurality of electrodes for delivering the electrical pulses from the plurality of conductors to the tissue of the patient; and
   the paddle including a tabbed portion extending in a direction of the width outward from the first side at the proximate end of the paddle, the tabbed portion extending in the direction of the width at an angle with respect to the longitudinal axis of the paddle, the tabbed portion for at least facilitating a user gripping the paddle at a position on the paddle offset from the longitudinal axis of the paddle.

2. The medical system of claim 1, where the tabbed portion extends from the proximate end of the paddle at an obtuse angle with respect to the longitudinal axis of the paddle and extending away from the proximal end and distal end.

3. The medical system of claim 1, where the tabbed portion extends from the proximate end of the paddle laterally in the direction of the width at a right angle with respect to the longitudinal axis of the paddle.

4. The medical system of claim 1, where the lead body is connected to the paddle at the tabbed portion of the paddle.

5. The medical system of 1, where the lead body is connected to the paddle at the tabbed portion of the paddle at an angle with respect to the longitudinal axis of the paddle.

6. The medical system of claim 1, where the tabbed portion includes at least one suture hole extending through the paddle to facilitate the securing of the paddle to the patient.

7. A medical lead system for delivering electrical stimulation to tissue of a patient, the medical lead system comprising:
   a lead body of an insulative material;
   a plurality of conductors extending through the lead body for conducting electrical pulses through the lead body;
   a elongated paddle having a distal end and proximate end, first side and a second side spaced apart by a width of the paddle, and a longitudinal axis extending between the distal end and the proximate end;
   a plurality of electrodes integrated with the paddle, with a portion of each of the plurality of electrodes being exposed at a face of the paddle, each of the plurality of electrodes being electrically connected to each of the plurality of conductors, the plurality of electrodes for delivering the electrical pulses from the plurality of conductors to the tissue of the patient; and
   the paddle including a tabbed portion extending in a direction of the width outward from the first side at the proximate end of the paddle, the tabbed portion extending in the direction of the width at least at a right angle with respect to the longitudinal axis of the paddle, the tabbed portion for at least facilitating a user gripping the paddle at a position on the paddle offset from the longitudinal axis of the paddle.

8. The medical system of claim 7, where the tabbed portion extends from the proximate end of the paddle at an obtuse angle with respect to the longitudinal axis of the paddle and extending away from the proximal end and distal end.

9. The medical system of claim 8, where the lead body is connected to the paddle at the tabbed portion of the paddle.

10. The medical system of 9, where the lead body is connected to the paddle at the tabbed portion of the paddle at an angle with respect to the longitudinal axis of the paddle.

11. The medical system of claim 10, where the tabbed portion includes at least one suture hole extending through the paddle to facilitate the securing of the paddle to the patient.

12. The medical system of claim 11, where the tabbed portion is generally arcuate in shape.

13. A medical lead system for delivering electrical stimulation to tissue of a patient, the medical lead system comprising:
   a lead body of an insulative material;
   a plurality of conductors extending through the lead body for conducting electrical pulses through the lead body;
   a elongated paddle having a distal end and proximate end, first side and a second side spaced apart by a width of the paddle, and a longitudinal axis extending between the distal end and the proximate end;
   a plurality of electrodes integrated with the paddle, with a portion of each of the plurality of electrodes being exposed at a face of the paddle, each of the plurality of electrodes being electrically connected to each of the plurality of conductors, the plurality of electrodes for delivering the electrical pulses from the plurality of conductors to the tissue of the patient; and
   the paddle including a tabbed portion extending in a direction of the width outward from one of the first side and the second side at the proximate end of the paddle, the tabbed portion extending in the direction of the width at least at a right angle with respect to the longitudinal axis of the paddle, the tabbed portion for at least facilitating a user gripping the paddle at a position on the paddle offset from the longitudinal axis of the paddle.

14. The medical system of claim 13, where the tabbed portion extends from the proximate end of the paddle at an obtuse angle with respect to the longitudinal axis of the paddle and extending away from the proximal end and distal end.

15. The medical system of claim 14, where the lead body is connected to the paddle at the tabbed portion of the paddle.

16. The medical system of 15, where the lead body is connected to the paddle at the tabbed portion of the paddle at an angle with respect to the longitudinal axis of the paddle.

17. The medical system of claim 16, where the tabbed portion includes at least one suture hole extending through the paddle to facilitate the securing of the paddle to the patient.

18. The medical system of claim 17, where the tabbed portion is generally arcuate in shape.

* * * * *